(12) United States Patent
Gu et al.

(10) Patent No.: US 8,913,012 B2
(45) Date of Patent: *Dec. 16, 2014

(54) OPTICAL MOUSE AND OPERATING METHOD THEREOF

(75) Inventors: Ren-Hau Gu, Hsin-Chu (TW);
Ming-Tsan Kao, Hsin-Chu (TW);
Sen-Huang Huang, Hsin-Chu (TW)

(73) Assignee: Pixart Imaging Inc., Hsin-Chu County (TW)

( * ) Notice: Subject to any disclaimer, the term of this patent is extended or adjusted under 35 U.S.C. 154(b) by 165 days.

This patent is subject to a terminal disclaimer.

(21) Appl. No.: 13/615,114

(22) Filed: Sep. 13, 2012

(65) Prior Publication Data
US 2013/0113705 A1    May 9, 2013

(30) Foreign Application Priority Data

Nov. 4, 2011   (TW) .............................. 100140264 A (51) Int. Cl.
*G09G 5/08*       (2006.01)
*G06F 3/033*     (2013.01)
(52) U.S. Cl.
CPC ..................................... *G06F 3/033* (2013.01)
USPC ......................................... 345/166; 345/163

(58) Field of Classification Search
USPC .................................................. 345/156–172
See application file for complete search history.

(56) References Cited

U.S. PATENT DOCUMENTS

| 5,867,148 | A | * | 2/1999 | Kamimaki et al. | ........... 345/169 |
| 7,072,701 | B2 | | 7/2006 | Chen et al. | |
| 2009/0015558 | A1 | * | 1/2009 | Hung | ........................ 345/163 |
| 2010/0033424 | A1 | * | 2/2010 | Kabasawa et al. | ........... 345/156 |
| 2010/0123655 | A1 | * | 5/2010 | Lai | ................................. 345/156 |

FOREIGN PATENT DOCUMENTS

| TW | 200912706 A | 3/2009 |
| TW | 201013472 A | 4/2010 |
| TW | 201032091 A | 9/2010 |

* cited by examiner

*Primary Examiner* — Premal Patel
(74) *Attorney, Agent, or Firm* — Lowe Hauptman & Ham, LLP (57) ABSTRACT

There is provided an operating method of an optical mouse including a first mode and a second mode. In the first mode, the optical mouse detects a finger displacement, a contact status and a physiological characteristic according to a plurality of image frames associated with a finger surface. In the second mode, the optical mouse calculates a mouse displacement according to a plurality of image frames associated with a work surface. There is further provided an optical mouse.

17 Claims, 7 Drawing Sheets

OPTICAL MOUSE AND OPERATING METHOD THEREOF

CROSS REFERENCE TO RELATED APPLICATION

This application claims the priority benefit of Taiwan Patent Application Serial Number 100140264, filed on Nov. 4, 2011, the full disclosure of which is incorporated herein by reference.

BACKGROUND

1. Field of the Disclosure

This disclosure generally relates to a human interface device and, more particularly, to an optical mouse that may detect both of a physiological characteristic of a user and a mouse displacement.

2. Description of the Related Art

As the optical finger mouse has a relatively small size, it is suitable for being applied to portable electronic devices. An optical finger mouse can be used to detect an intensity variation of reflected light from a finger surface of a user so as to accordingly identify a finger contact status and a finger displacement with respect to a touch surface. However, with the development of industry, users spend more and more time on utilizing various portable electronic devices that puts a lot of stress on their bodies. Therefore, if a portable electronic device also has the function of detecting physiological characteristics of a user and is able to give a warning when necessary, the overuse of the portable electronic devices can then be avoided.

Conventional pulse oximeters utilize a noninvasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variation of the penetrating light of the two wavelengths is detected, the blood oxygenation can be calculated according to equation (1):

$$\text{Oxygen saturation} = 100\% \times [HbO_2]/([HbO_2]+[Hb]) \quad (1)$$

wherein $[HbO_2]$ is an oxyhemoglobin concentration; and $[Hb]$ is a deoxyhemoglobin concentration.

Figure 1:
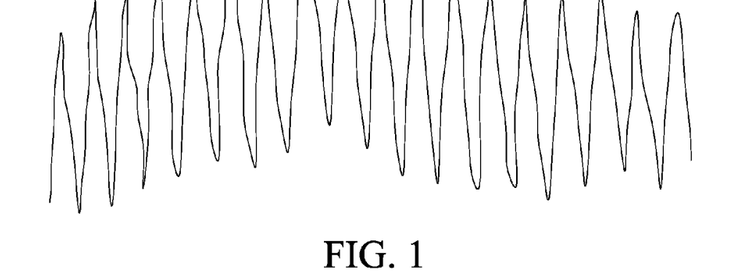
FIG. 1 shows a schematic diagram of an intensity variation of the penetrating light detected by pulse oximeters.

Generally, the intensity variation of the penetrating light of the two wavelengths detected by a pulse oximeter is similar to FIG. 1. This is because blood vessels will expand and contract with heartbeats such that the blood volume that the light beams pass through will change to accordingly change the ratio of light energy being absorbed. Therefore, the absorptivity of blood of different light spectra can be calculated according to the intensity information changing continuously so as to calculate the physiology information, e.g. the oxyhemoglobin and deoxyhemoglobin concentration, respectively. Finally, the blood oxygenation can be calculated according to equation (1).

However, as conventional pulse oximeters detect the intensity variation of the penetrating light, different intensity signals will be detected by detecting different parts of the human body. In addition, when the part of the human body being detected has a movement, a disturbed signal can be detected such that it is not possible to calculate correct physiology information. Therefore, conventional pulse oximeters cannot be applied to electronic devices operated in a moving state.

Accordingly, the present disclosure provides an optical mouse that may detect both of a physiological characteristic of a user and a mouse displacement, and the signal noise caused by the finger movement can be eliminated when detecting the physiological characteristic.

SUMMARY

It is an object of the present disclosure to provide an optical mouse and operating method thereof that may detect a finger displacement, a finger contact status and a physiological characteristic of a user by analyzing reflected light from a finger, and calculate a mouse displacement of the optical mouse by analyzing reflected light from a work surface.

It is another object of the present disclosure to provide a mouse chip that may detect a finger displacement, a finger contact status and a physiological characteristic of a user by analyzing reflected light from a finger, and calculate a mouse displacement of the optical mouse by analyzing reflected light from a work surface so as to output encoded, sequenced and/or compressed finger information, physiology information and mouse displacement information.

It is another object of the present disclosure to provide an optical mouse and operating method thereof that may detect a finger displacement, a finger contact status, a physiological characteristic of a user and a mouse displacement, and has a mechanism of eliminating the interference from ambient light sources.

It is another object of the present disclosure to provide an optical mouse and operating method thereof that may detect a finger displacement, a finger contact status, a physiological characteristic of a user and a mouse displacement, and has the denoising mechanism.

It is another object of the present disclosure to provide an optical mouse and operating method thereof that may detect a finger displacement, a finger contact status, a physiological characteristic of a user and a mouse displacement, and may enter a sleep mode after idling for a predetermined time period.

It is another object of the present disclosure to provide an optical mouse and operating method thereof that may detect a finger displacement, a finger contact status, a physiological characteristic of a user and a mouse displacement, and the physiological characteristic may be abandoned or may not be calculated if the finger displacement is too large.

The present disclosure provides an optical mouse configured to detect a physiological characteristic of a finger or a mouse displacement of the optical mouse with respect to a work surface. The optical mouse includes at least two light sources, a light control unit, at least one image sensor and a processing unit. The at least two light sources emits light of different wavelengths to the finger and the work surface. The light control unit is configured to control the light sources. The at least one image sensor is configured to capture reflected light from the finger to generate a plurality of image frames associated with the finger and capture reflected light from the work surface to generate a plurality of image frames associated with the work surface. The processing unit is configured to calculate the physiological characteristic according to the image frames associated with the finger and calculate the mouse displacement according to the image frames associated with the work surface.

The present disclosure further provides an operating method of an optical mouse switching between a first mode and a second mode using a switching unit. The operating method includes: in the first mode, calculating a physiological characteristic according to a plurality of image frames associated with a finger surface using the optical mouse; and in the second mode, calculating a mouse displacement according to a plurality of image frames associated with a work surface using the optical mouse.

The present disclosure further provides an optical mouse includes an optical finger mouse, an optical navigation device and a switching unit. The optical finger mouse is configured to detect at least one of a blood oxygenation and a heart rate of a finger. The optical navigation device is configured to detect a mouse displacement of the optical mouse with respect to a work surface. The switching unit is configured to switch the optical mouse to operate between the optical finger mouse and the optical navigation device.

The optical mouse of the present disclosure further includes at least one light guide configured to direct the light emitted by the light sources to the finger surface and/or the work surface.

In the optical mouse and the operating method of the optical mouse of the present disclosure, the physiological characteristic may include a blood oxygenation and a heart rate. In the present disclosure, the finger movement informant and the physiology information are separated by means of independent component analysis (ICA) or blind source separation (BSS) so as to effectively eliminate the signal noise caused by the finger movement.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 2A:
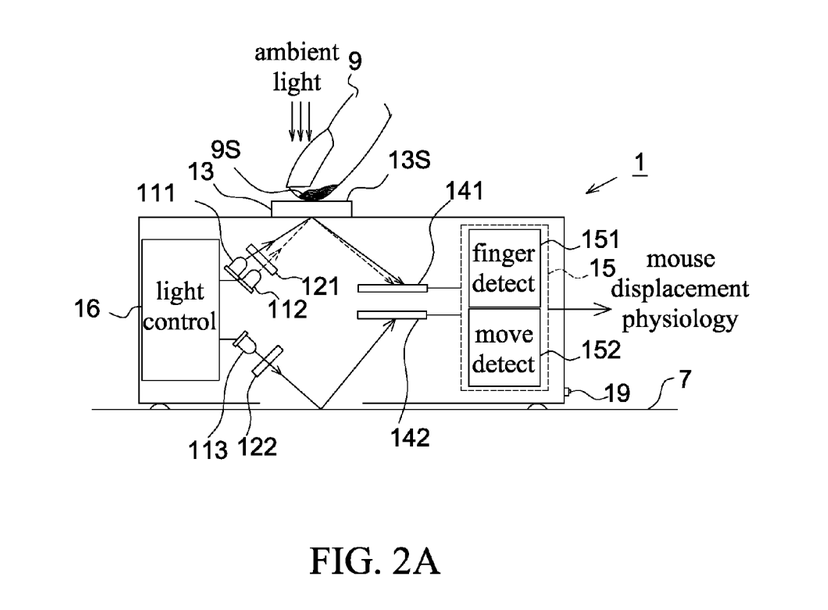
FIG. 2A shows a schematic diagram of the optical mouse according to an embodiment of the present disclosure.

Please refer to FIG. 2A, it shows a schematic diagram of the optical mouse 1 according to an embodiment of the present disclosure. The operating method of the optical mouse 1 includes a first mode and a second mode, and a switching unit is configured to switch between the first mode and the second mode. The first mode is configured to detect a finger displacement, a contact status of a finger 9 of a user with respect to the optical mouse 1 and a physiological characteristic of the user, wherein the physiological characteristic may include a blood oxygenation and a heart rate. The second mode is configured to detect a mouse displacement of the optical mouse 1 with respect to a work surface 7. In this embodiment, the optical mouse 1 performs the finger detection (i.e. switching from the second mode to the first mode) when the optical mouse 1 is at rest for a predetermined time interval, when the image quality of the image frames associated with the work surface 7 is lower than a predetermined value or when the switching unit is triggered by the user. In the first mode, the optical mouse 1 starts to detect the finger displacement and the physiological characteristic when identifying that the contact status is a touch state (i.e. the finger 9 touches the optical mouse 1).

In FIG. 2A, the optical mouse 1 includes three light sources 111-113, two light guides 121-122 (the number of the light guides herein is only exemplary), a touch member 13, two image sensors 141-142, a processing unit 15, a light control unit 16 and a switching unit 19. It should be mentioned that the spatial relationship between every component in FIG. 2A is only exemplary and not to limit the present disclosure. The light sources 111-113 may be light emitting diodes or laser diodes, wherein the light sources 111 and 112 respectively emit light of different wavelengths to the finger surface 9S. Preferably, said different wavelengths are the two wavelengths used in conventional pulse oximeters, e.g. red light of wavelength about 660 nm and infrared light of wavelength about 905, 910 or 940 nm The light source 113 preferably emits light, e.g. red light or blue light, of a wavelength shorter than the wavelengths of light emitted by the light sources 111 and 112 to the work surface 7. In this embodiment, the light sources 111 and 112 are for the finger detection, and the light source 113 is for the mouse displacement detection. It is appreciated that the wavelengths mentioned herein are the center wavelength of respective illumination spectrum of the light sources 111-113.

The light guide 121 is configured to direct the light emitted by the light sources 111 and 112 to the touch member 13, and the light guide 122 is configured to direct the light emitted by the light source 113 to the work surface 7 (e.g. through an opening on the bottom surface of the optical mouse 1), wherein the structure and the light guiding mechanism of the light guides 121 and 122 do not have any limitation as long as the light guiding function can be implemented. In other embodiments, if the light emitted from the light sources 111-113 can directly impinge on the touch member 13 and the work surface 7, the light guides 121 and 122 may not be implemented.

The touch member 13 has a touch surface 13S for the finger 9 to operate thereon, and the touch member 13 is preferably transparent to the light emitted by the light sources 111 and 112 such that when the finger 9 approaches or touches the touch surface 13S, the light emitted by the light sources 111 and 112 is reflected. It is appreciated that an area of the touch surface 13S may be larger or smaller than that of the finger surface 9S.

The image sensor 141 receives, with a sampling parameter, reflected light from the touch member 13 (more specifically from the finger surface 9S) to generate a plurality of image frames, which may have a size of 16×16, wherein the sampling parameter may include an exposure time and an image gain, but not limited thereto. The image sensor 142 captures, at a sampling frequency, reflected light from the work surface 7 to generate a plurality of image frames, wherein the sampling frequency may be those used in a general optical mouse. The image sensor 141 is preferably an active matrix sensor, e.g. a CMOS image sensor, and the image sensor 142 may be a CCD image sensor or a CMOS sensor, wherein the image sensors 141 and 142 may be other devices configured to sense image frames.

The processing unit 15 detects a finger displacement, a contact status of the finger 9 with respect to the touch surface 13S and a physiological characteristic of the user according to the plurality of image frames associated with the finger 9 outputted by the image sensor 141 (i.e. the first mode), or calculates a mouse displacement of the optical mouse 1 with respect to the work surface 7 according to the plurality of image frames associated with the work surface 7 outputted by the image sensor 142 (i.e. the second mode). The finger displacement, contact status, physiological characteristic and mouse displacement obtained by the processing unit 15 may be sent to an electronic device having at least one response unit for displaying or for corresponding control, wherein the response unit may be a display device, a lamp device, a seven-segment display and/or a sound device. The electronic device may be a portable electronic device or a home appliance.

The light control unit 16 is coupled to the processing unit 15 and configured to control on-states and off-states of the light sources 111-113 corresponding to the image capturing of the image sensors 141 or 142, and details thereof will be described hereinafter.

In this embodiment, the light sources 111 and 112, the image sensor 141, the processing unit 15 (or a finger detection unit 151) and the light control unit 16 are served as an optical finger mouse configured to detect a contact status, a finger displacement and a physiological characteristic of the finger 9. The light source 113, the image sensor 142, the processing unit 15 (or a displacement detection unit 152) and the light control unit 16 are served as an optical navigation device configured to detect a mouse displacement of the optical mouse 1 with respect to the work surface 7. The switching unit 19 switches the optical mouse 1 to operate as the optical finger mouse or the optical navigation device.

Figure 2B:
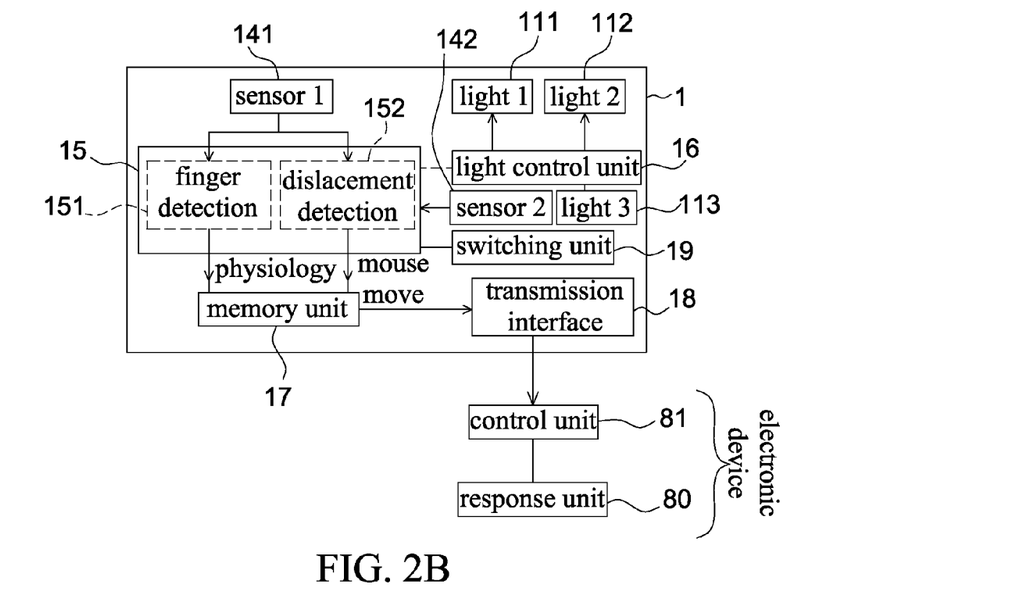
FIG. 2B shows a schematic block diagram of the optical mouse according to an embodiment of the present disclosure.

Please refer to FIGS. 2A and 2B, FIG. 2B shows a schematic block diagram of the optical mouse 1 according to an embodiment of the present disclosure. The optical mouse 1 includes a first light source 111, a second light source 112, a third light source 113, an image sensor 141, an image sensor 142, the processing unit 15, the light control unit 16, a memory unit 17, a transmission interface 18 and the switching unit 19, wherein because the processing unit 15 has multifunction, the processing unit 15 may further include a finger detection unit 151 configured to detect the finger displacement, contact status and physiological characteristic of the finger 9 with respect to the touch surface 13S and include a displacement detection unit 152 configured to detect the mouse displacement of the optical mouse 1 with respect to the work surface 7. That is, the processing unit 15 may be a single element or composed of two elements.

The first light source 111 may emit red light of wavelength about 660 nm to the finger 9, and the second light source 112 may emit infrared light of wavelength about 905, 910 or 940 nm to the finger 9. Broadly speaking, the first light source 111 and the second light source 112 respectively emit light of the two wavelengths used in conventional pulse oximeters. The third light source 113 may emit light, e.g. red light or blue light, of a wavelength shorter than the wavelengths of light emitted by the light sources 111 and 112 to the work surface 7. Functions of the image sensor 141, the image sensor 142 and the light control unit 16 are described above and thus details thereof are not repeated herein. The memory unit 17 is configured to store the finger displacement, contact status, physiological characteristic and mouse displacement obtained by the processing unit 15 and to store various parameters needed in the calculation. The transmission interface 18 is configured to wired or wirelessly transmit the finger displacement, contact status, physiological characteristic and mouse displacement stored in the memory unit 17 to a control unit 81, wherein the wired and wireless communications are well known and thus details thereof are not described herein. The control unit 81 may be integrated in or separated from an electronic device having at least one response unit 80 and configured to control the electronic device to display and/or respond the received finger displacement, contact status, physiological characteristic and mouse displacement by means of the response unit 80. The switching unit 19 is configured to switch an operating mode of the optical mouse 1, e.g. to switch the processing unit 15 to detect the finger displacement, contact status and physiological characteristic according to the plurality of image frames associated with the finger 9 in a first mode or to switch the processing unit 15 to detect the mouse displacement according to the plurality of image frames associated with the work surface 7 in a second mode, wherein the switching unit 19 may be implemented by a mechanical switch or an electronic switch. The mechanical switch may be controlled by a user to switch between two operating modes. The electronic switch may switch the second mode to the first mode when the processing unit 15 identifies that the optical mouse 1 is at static (i.e. the mouse displacement is 0) over a predetermined time interval or that the image quality of the image frames associated with the work surface 7 is lower than a predetermined value (e.g. the optical mouse 1 is lifted from the work surface 7), and may switch the first mode to the second mode when the processing unit 15 identifies that the optical mouse 1 starts to move with respect to the work surface 7.

The optical mouse 1 of the present disclosure may incorporate with an electronic device having a response unit 80 such that a user may control a cursor shown on the response unit 80 or a software executed by the electronic device through the optical mouse 1, and the electronic device may show the physiological characteristic of the user for reference when the switching unit 19 of the optical mouse 1 is triggered and give a warning when the physiological characteristic indicates that the user is in a fatigue state (e.g. according to a value of the physiological characteristic), wherein the method of showing the physiological characteristic and the warning may be implemented by, for example, showing on a screen, representing by a lamp device or by sound using a software.

For example, when the optical mouse 1 is switched to the second mode, the light control unit 16 controls the third light source 113 to emit light, and the image sensor 142 receives reflected light from the work surface 7 and outputs image frames. The processing unit 15 (or the displacement detection unit 152) calculates a mouse displacement of the optical mouse 1 with respect to the work surface 7, wherein the method of calculating the mouse displacement may use the correlation between images, the blocking matching, the motion detection algorithm or the like. Finally, the optical mouse 1 outputs the calculated mouse displacement.

For example, when the optical mouse 1 is switched to the first mode, the light control unit 16 controls the first light source 111 and the second light source 112 to emit light, and the image sensor 141 receives reflected light from the finger surface 9S and outputs image frames. The processing unit 15 (or the finger detection unit 151) detects a finger displacement and a contact status of the finger surface 9S with respect to the touch member 13 and a physiological characteristic. Finally, the optical mouse 1 outputs the calculated finger displacement, contact status and physiological characteristic. In other embodiments, the optical mouse 1 may include two image sensors configured to detect light of two different wavelengths respectively emitted by the light sources 111 and 112 (i.e. the image sensor 141 is replaced by two image sensors), wherein an optical bandpass filter may be integrated on one or two of the image sensors in order to select the desired spectrum.

Since the processing unit 15 may use conventional methods to calculate the mouse displacement (i.e. the process of the second mode), details thereof are not described herein. Only the methods of calculating the finger displacement, contact status and physiological characteristic by the processing unit 15 will be described hereinafter; that is, only the operations of the light sources 111 and 112, the image sensor 141, the processing unit 15 (or the finger detection unit 151) and the light control unit 16 (i.e. the first mode) are described herein.

Sampling Mechanism

The first mode of the present disclosure utilizes two light sources 111 and 112 and may perform two functions simultaneously, wherein the function of detecting the finger displacement and contact status may use the image frames associated with any wavelength without limitation, but the function of detecting the physiological characteristic needs to be respectively performed corresponding to the image frames of different wavelengths. First, the sampling mechanism of the image frames in the present disclosure is illustrated hereinafter.

Figure 3:
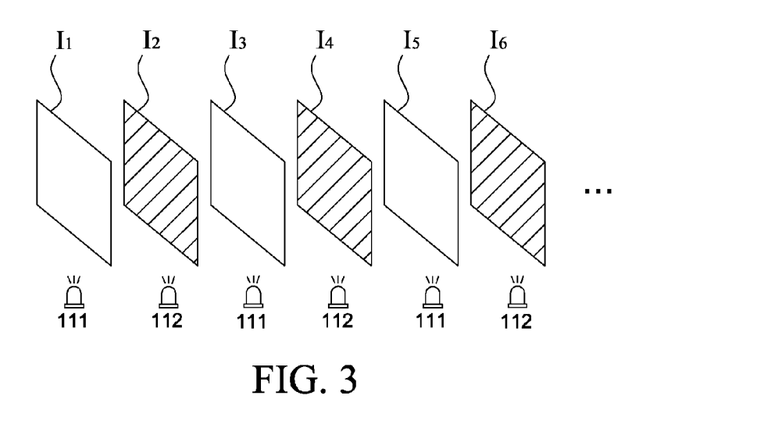
FIG. 3 shows a schematic diagram of the image frames associated with the finger captured by the image sensor of the optical mouse according to the embodiment of the present disclosure.

In one embodiment, the light control unit 16 controls the first light source 111 and the second light source 112 to turn on alternatively. The image sensor 141 captures image frames at a high and fixed sampling frequency (e.g. 3,000 frames/sec) and synchronizing to the turning on (i.e. on-states) of the first light source 111 or the second light source 112, and outputs a plurality of image frames $I_1$ to $I_6$... as shown in FIG. 3 to the processing unit 15 (or the finger detection unit 151), wherein the image frames $I_1$ to $I_6$ ... include first image frames $I_1$, $I_3$, $I_5$ ... corresponding to the on-states of the first light source 111 and second image frames $I_2$, $I_4$, $I_6$ ... corresponding to the on-states of the second light source 112.

The processing unit 15 may identify a contact status and calculate a finger displacement according to the first and second image frames $I_1$ to $I_6$ ..., e.g. identifying whether the finger 9 approaches or touches the touch surface 13S according to a comparison result of comparing a brightness value of the first and second image frames with at least one brightness threshold, wherein when the brightness value of the image frames is larger or smaller than the brightness threshold, a touch state is entered. After entering the touch state, the processing unit 15 may calculate the finger displacement according to the correlation between two first image frames, between one first image frame and one second image frame, or between two second image frames. It should be mentioned that although the method of identifying the contact status and calculating the finger displacement may use conventional methods, the identification process and the calculation process in the present disclosure need to use the image frames corresponding to the reflected light of two different wavelengths and thus are different from conventional navigation devices.

The processing unit 15 may calculate an intensity variation of first image frame according to the first image frames $I_1$, $I_3$, $I_5$ ..., and calculate an intensity variation of second image frame according to the second image frames $I_2$, $I_4$, $I_6$ ... (described later), and accordingly calculate the absorptivity of blood in two spectra so as to obtain $[HbO_2]$ and $[Hb]$. Finally, the blood oxygenation may be calculated according to equation (1), and the heart rate may also be calculated according to a comparison result of comparing the intensity variation of first image frame and/or the intensity variation of second image frame with at least one pulse threshold.

Figure 4:
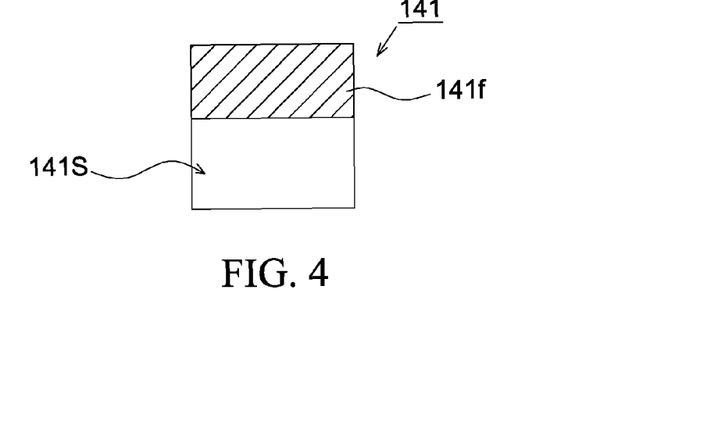
FIG. 4 shows a schematic diagram of the image sensor of the optical mouse according to the embodiment of the present disclosure, wherein an optical filter is disposed in front of a part of a sensing surface thereof.

In another embodiment, the light control unit 16 controls the first light source 111 and the second light source 112 to turn on simultaneously and synchronizing to the image capturing of the image sensor 141; that is, the image sensor 141 may receive reflected light of two wavelengths simultaneously. Therefore, in this embodiment an optical filter 141$f$ is further disposed in front of at least a part of a sensing surface 141S of the image sensor 141 as shown in FIG. 4, wherein the optical filter 141$f$ may be an optical bandpass filter to allow the part of the sensing surface 141S behind the optical filter 141$f$ to only receive the spectrum of light of the first light source 111 or the second light source 112 such that the processing unit 15 may distinguish the first image frame (i.e. the part of the image frame associated with the first light source 111) and the second image frame (i.e. the part of the image frame associated with the second light source 112). It is appreciated that in the present disclosure the position and the area of the optical filter 141$f$ are not limited to those shown in FIG. 4.

In this manner, the processing unit 15 may also calculate a contact status and a finger displacement according to the first and second image frames $I_1$ to $I_6$ .... The processing unit 15 may also calculate the intensity variation of first image frame according to the first image frames $I_1$, $I_3$, $I_5$ ..., calculate the intensity variation of second image frame according to the second image frames $I_2$, $I_4$, $I_6$ ..., and calculate at least one of the blood oxygenation and the heart rate according to the two intensity variations.

It is appreciated that as the sensing efficiency of the image sensor 141 toward light of different wavelengths may be different or the illumination brightness values of the first light source 111 and the second light source 112 may not be exactly identical, the brightness value of the image frames captured by the image sensor 141 may be previously adjusted (e.g. by adjusting the sampling parameter, such as an exposure time and an image gain, of the image frames corresponding to different wavelengths) before the shipment of the optical mouse 1 such that the image frames initially outputted by the image sensor 141 may have substantially identical brightness values to eliminate the possibility of error.

In this embodiment, the light control unit 16 controls the first light source 111 and the second light source 112 such that the image sensor 141 captures reflected light from the finger 9 at a sampling frequency to generate a plurality of first image frames corresponding to on-states of the first light source and a plurality of second image frames corresponding to on-states of the second light source. The processing unit 15 calculates the contact status, finger displacement and physiological characteristic according to the first image frames and the second image frames.

Mechanism of Eliminating Ambient Light Interference

In FIG. 2A, as the touch member 13 and the finger 9 are light transmissive, the ambient light outside the optical mouse 1 can penetrate the finger 9 and the touch member 13 and then be received by the image sensor 141 to degrade the image quality of the image frames captured thereby. In the present disclosure, the light control unit 16 may control the first light source 111 and the second light source 112 to turn off (i.e. the off-state) in predetermined time intervals.

Figure 5:
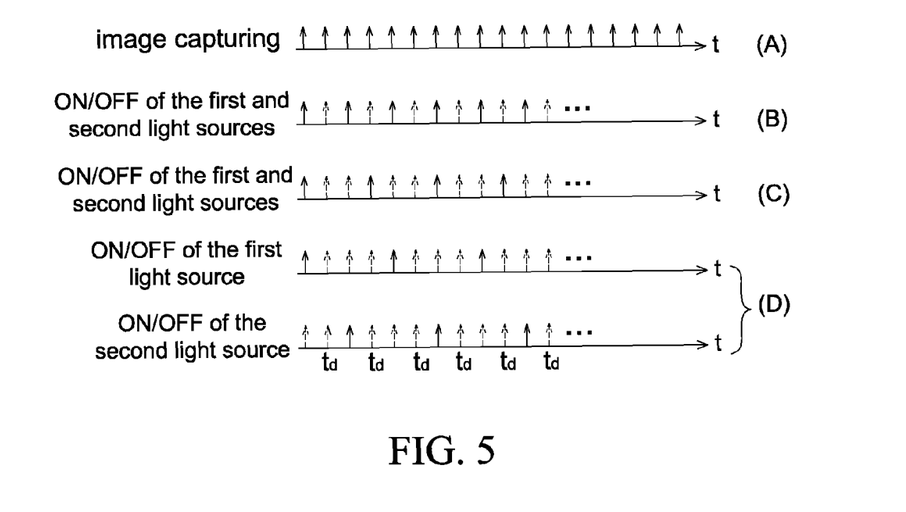
FIG. 5 shows a schematic diagram of the image capturing of the image frames associated with the finger and the ON/OFF of the light source in the optical mouse according to the embodiment of the present disclosure.

For example please refer to FIG. 5, it shows a schematic diagram of the image capturing of the image sensor 141 and the ON/OFF of the first light source 111 and the second light source 112, wherein in FIGS. 5(B)-5(D) solid arrows denote the on-states of the light sources (or lighting at a first brightness value) and dashed arrows denote the off-states of the light sources (or lighting at a second brightness value). FIG. 5(A) shows that the image sensor 141 captures image frames at a fixed sampling frequency. FIG. 5(B) shows that the first light source 111 and the second light source 112 are alternatively turned on and turned off at the same time, and thus the image sensor 141 may alternatively capture bright image frames (i.e. corresponding to the on-states of the light sources) and dark image frames (i.e. corresponding to the off-states of the light sources). FIG. 5(C) shows that the first light source 111 and the second light source 112 are simultaneously turned on once after being turned off two image periods, and this embodiment is generally for a lower finger displacement. As mentioned above, when the first light source 111 and the second light source 112 are turned on simultaneously, e.g. FIGS. 5(B) and 5(C), the image sensor 141 further includes an optical filter 141$f$ (as shown in FIG. 4) for spatially distinguishing the image frame associated with different light sources such that one part of the image sensor 141 may sense reflected light associated with the first light source 111 and the other part thereof may sense reflected light associated with the second light source 112.

When the finger 9 touches or approaches the touch surface 13S, the bright image frames, which are associated with the on-states of the light sources, include components of (reflected light from finger+stray light+ambient light), and the dark image frames, which are associated with the off-states of the light sources, include only the component of (ambient light). Therefore, if a dark image frame is subtracted from a bright image frame, the interference from the ambient light can be effectively eliminated. The processing unit 15 may calculate the finger displacement, contact status and physiological characteristic according to differential images between the bright image frames and the dark image frames.

Please refer to FIG. 5(D), it shows an embodiment in which the first light source 111 and the second light source 112 are turned on alternatively. In this embodiment, in order to allow the image sensor 141 to be able to capture dark image frames, the light control unit 16 controls the first light source 111 and the second light source 112 to alternatively turn on every other image frame, e.g. the two light sources are both turned off at time $t_d$ in FIG. 5(D). Accordingly, the processing unit 15 may calculate a differential first image (i.e. bright first image frame—dark image frame) and a differential second image (i.e. bright second image frame—dark image frame), and calculate the finger displacement, contact status and physiological characteristic according to the differential first and second images. As mentioned above, if the first light source 111 and the second light source 112 are turned on alternatively, the image sensor 141 temporally distinguishes the image frames associated with different light sources.

In this embodiment, the light control unit 16 controls the first light source 111 and the second light source 112 to turn on simultaneously or alternatively and the image sensor 141 is able to capture dark image frames when both the light sources are turned off. The interference from ambient light is eliminated by calculating a difference between the bright image frame and the dark image frame. It is appreciated that the on-states and the off-states of each light source shown in FIG. 5 are only exemplary and not to limit the present disclosure.

Denoising Mechanism

As the image frames captured by the image sensor 141 generally include noise which is randomly distributed in the image frames being captured. Therefore, in the present disclosure it is able to calculate a sum of M image frames to increase the signal-to-noise ratio (SNR) thereby improving the calculation accuracy of the physiological characteristic. For example, it is able to calculate a sum of 10 image frames and two groups of 10 image frames may have partially repeated image frames or totally different 10 image frames. It is appreciated that if the first light source 111 and the second light source 112 are turned on alternatively, the sum of image frames in this embodiment may be a sum of the first image frames (e.g. $I_1+I_3+I_5+\ldots$ as shown in FIG. 3) and a sum of the second image frames (e.g. $I_2+I_4+I_6+\ldots$ as shown in FIG. 3) since two intensity variations need to be calculated respectively. However, if the first light source 111 and the second light source 112 are turned on simultaneously, the sum of image frames in this embodiment is a sum of successive image frames (e.g. $I_1+I_2+I_3+I_4+I_5+I_6+\ldots$ as shown in FIG. 3), and the two intensity variations may be spatially distinguished by post-processing. In addition, if the mechanism of eliminating ambient light interference described above is incorporated in this embodiment, the sum of image frames in this embodiment is a sum of the differential images; that is, the process of eliminating ambient light interference is performed and then the process of denoising is performed successively. In other embodiments, only one of the mechanism of eliminating ambient light interference and the denoising mechanism is performed.

As mentioned above, the image sensor 141 may capture image frames with different sampling parameters at different conditions, e.g. the image sensor 141 may have different absorption of light at different wavelengths. Therefore different sampling parameters, such as different exposure times and different image gains, may be used to make the first image frames and the second image frames have substantially identical initial brightness values in order to correctly perform the post-processing on the image frames; that is, the sampling parameters associated with the first image frames and the second image frames may be different. In the present disclosure, in order to eliminate the influence of different sampling parameters, every image frame or the sum of M image frames or the average of M image frames may be normalized by the sampling parameter, e.g. (a sum of M image frames/sampling parameter) or (an average of M image frames/sampling parameter), wherein M is a positive integer.

Calculating Physiological Characteristics

Corresponding to the on-states of different light sources, the image frames captured by the image sensor 141 may contain physiology information and finger movement information at the same time. Therefore, in the present disclosure the processing unit 15 (or the finger detection unit 151) has to separate two types of information at first and then is able to calculate the physiological characteristic correctly. In the present disclosure, the processing unit 15 may separate the two types of information according to, for example, independent component analysis (ICA) or blind source separation (BSS).

Figure 6:
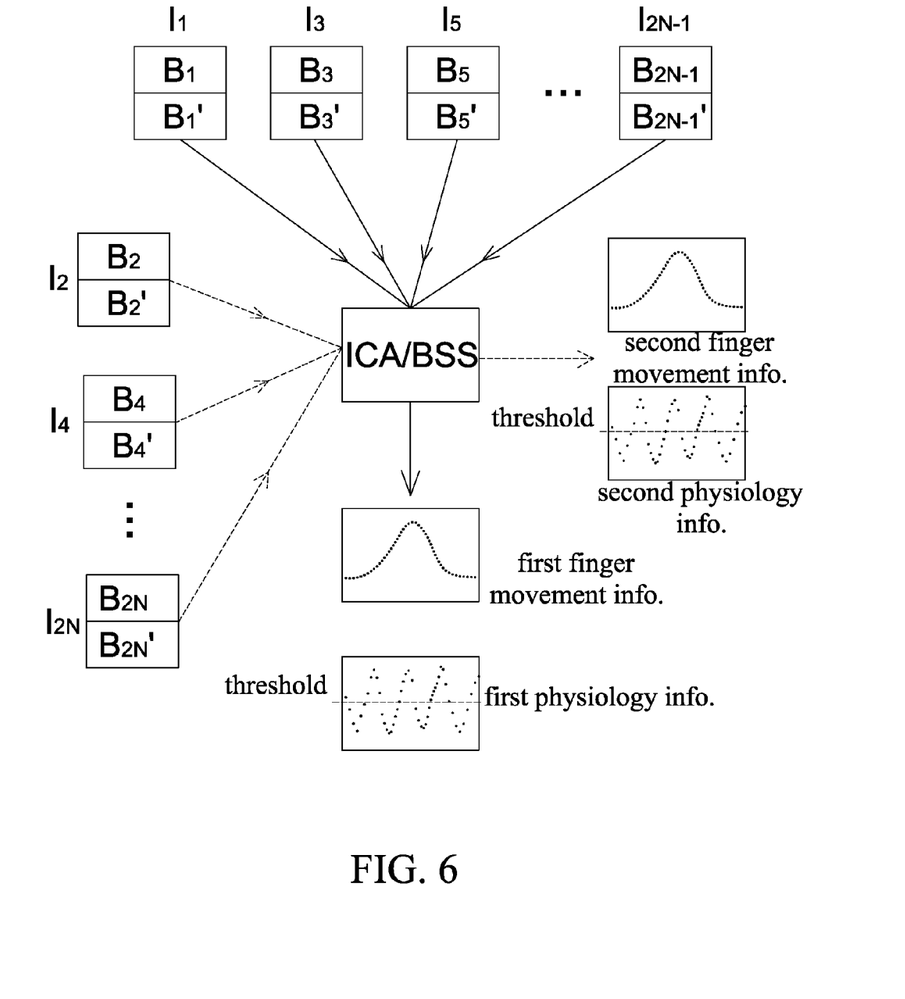
FIG. 6 shows a schematic diagram of separating the finger movement information and the physiology information by the processing unit of the optical mouse according to the embodiment of the present disclosure.

Please refer to FIGS. 3 and 6, taking the first image frames $I_1, I_3, I_5 \ldots$ shown in FIG. 3 as an example, each of the first image frames (e.g. original first image frames or the first image frames processed by the mechanism of eliminating ambient light interference and/or normalizing mechanism) or each of the sum of a plurality of first image frames (e.g. a sum of M original first image frames or a sum of M first image frames processed by the mechanism of eliminating ambient light interference and/or normalizing mechanism) is divided into at least two parts and an average brightness of each part is calculated, e.g. the image frame $I_1$ is divided into two parts respectively having an average brightness $B_1$ and $B_1'$; the image frame $I_3$ is divided into two parts respectively having an average brightness $B_3$ and $B_3'$; . . . ; the image frame $I_{2N-1}$ is divided into two parts respectively having an average brightness $B_{2N-1}$ and $B_{2N-1}'$, wherein the image frames may be divided into more than two parts in other embodiments. Next, a first finger movement informant and a first physiology information is separated from the divided image frames according to independent component analysis (ICA) or blind source separation (BSS) method as shown in FIG. 6, and each of the information is shown as a curve of intensity variation. In the present disclosure the finger movement information is abandoned and the physiological characteristic is calculated only according to the physiology information (i.e. the intensity variation of image frame). It is appreciated that as the sampling frequency of the image sensor 141 is much higher than the heart rate, the separated physiology information is shown as a curve of the intensity variation in accordance with the pulse beating (i.e. similar to FIG. 1), but the separated finger movement information is not limited to that shown in FIG. 6. In addition, the two parts divided from the image frames are not necessary to be the upper and the lower parts of the image frames. In addition, as it is necessary to respectively calculate the physiology information associated with two different wavelengths, the aforementioned separation process is performed respectively on the first image frames $I_1$, $I_3$, $I_5$ . . . (i.e. corresponding to the on-state of the first light source) and the second image frames $I_2$, $I_4$, $I_6$ . . . (i.e. corresponding to the on-state of the second light source) such that second finger movement information and second physiology information can be retrieved from the second image frames $I_2$, $I_4$, $I_6$ . . . . It should be mentioned that, if the information separation is performed on the sum or average of the image frames, each of $I_1$ to $I_{2N-1}$ and $I_2$ to $I_{2N}$ shown in FIG. 6 represents a sum or an average of M image frames.

It should be mentioned that the finger displacement and the contact status of the finger 9 are calculated by the processing unit 15 directly according to the original first image frames and second image frames without using the separated finger movement information. The ICA and BSS methods are mainly configured to separate combined signals. When the separated finger movement information is abandoned, it is able to eliminate the signal noise caused by the finger movement.

In the present disclosure, the processing unit 15 further calculates a heart rate according to a comparison result of comparing at least one pulse threshold with a first intensity variation (i.e. the first physiology information) and/or a second intensity variation (i.e. the second physiology information).

Sleep Mode

The optical mouse 1 of the present disclosure may enter a sleep mode after idling for a predetermined time period. For example, when the processing unit 15 identifies that a finger 9 does not approach or touch the touch surface 13S within the predetermined time period, the sleep mode is entered.

Mechanism of Removing Physiological Characteristic

Although the processing unit 15 of the optical mouse 1 of the present disclosure may calculate the finger displacement and the physiological characteristic simultaneously, accurate physiological characteristics are preferably obtained when the finger displacement is relatively small. Therefore, in the present disclosure the processing unit 15 may previously identify whether the finger displacement is larger than a predetermined value (i.e. a displacement threshold). When the finger displacement is larger than the predetermined value, the image frames captured by the image sensor 141 are only used to calculate the finger displacement or to identify the contact status but not used to calculate the physiological characteristic; or even though the physiological characteristic is calculated, the physiological characteristic is directly removed from the memory unit 17 without being sent by the transmission interface 18. The predetermined value may be determined according to different applications, e.g. according the size of the sensing surface and/or the searching block, but not limited thereto.

Figure 7:
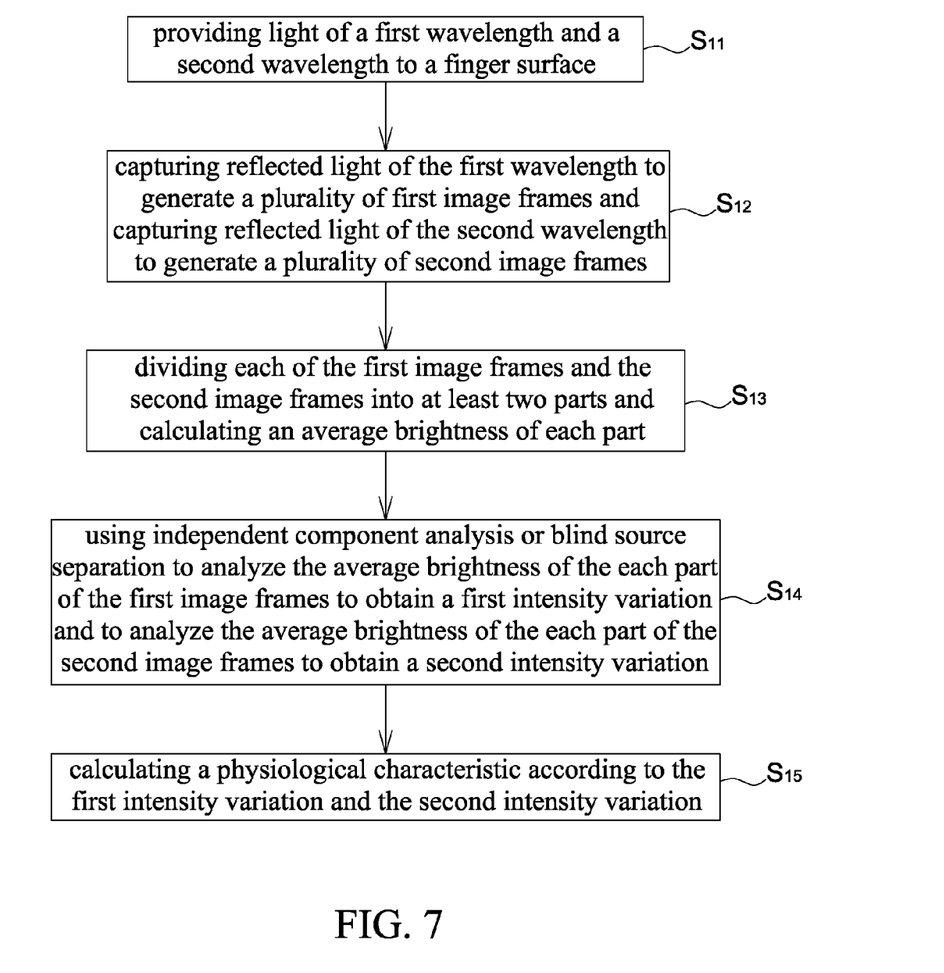
FIG. 7 shows a flow chart of the physiology detection method according to an embodiment of the present disclosure.

The physiology detection method of the optical mouse 1 according to reflected light from the finger surface includes the steps of: providing light of a first wavelength and a second wavelength to a finger surface (Step $S_{11}$); capturing reflected light of the first wavelength to generate a plurality of first image frames and capturing reflected light of the second wavelength to generate a plurality of second image frames (Step $S_{12}$); dividing each of the first image frames and the second image frames into at least two parts and calculating an average brightness of each part (Step $S_{13}$); using independent component analysis or blind source separation to analyze the average brightness of the each part of the first image frames to obtain a first intensity variation and to analyze the average brightness of the each part of the second image frames to obtain a second intensity variation (Step $S_{14}$); and calculating a physiological characteristic according to the first intensity variation and the second intensity variation (Step $S_{15}$). Details of every step have been described above and thus are not repeated herein.

Figure 8:
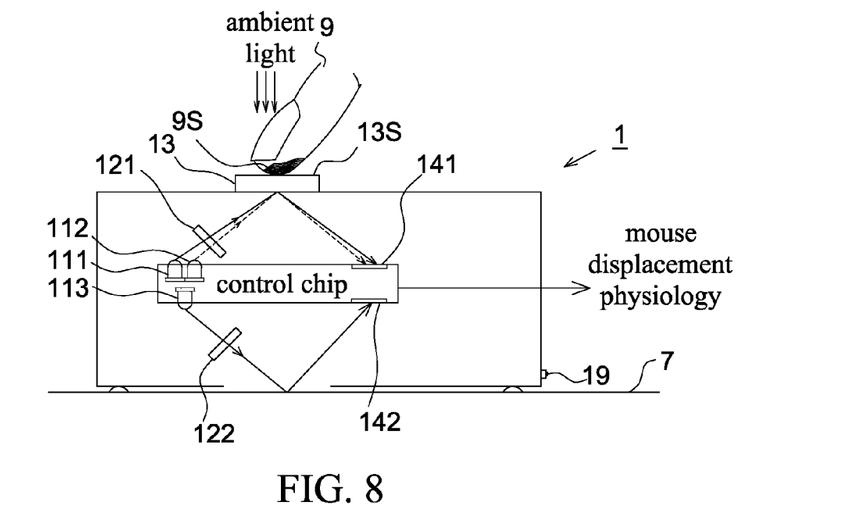
FIGS. 8-10 show schematic diagrams of the optical mouse according to alternative embodiments of the present disclosure.

In another embodiment, a part of or all of the light sources 111-113, the image sensors 141 and 142, the processing unit 15, the light control unit 16, the memory unit 17, the transmission interface 18 and the switching unit 19 may be manufactured as a mouse chip or a package as shown in FIG. 8. The mouse chip is configured to calculate the mouse displacement of the optical mouse 1 with respect to the work surface 7 or to detect the finger displacement, contact status and physiological characteristic of the finger 9 according to different operating modes, and to output encoded, sequenced and/or compressed finger displacement, contact status, physiological characteristic and mouse displacement (said encoding process, sequential process and/or compression process may be performed by the transmission interface or by an additional communication unit), wherein the methods of calculating the finger displacement, contact status and physiological characteristic have been described above and thus details thereof are not repeated herein. In other words, the optical finger mouse and the optical navigation device included in the optical mouse of the present disclosure may be packaged as a control chip so as to calculate the mouse displacement of the optical mouse 1 with respect to the work surface 7 or the finger displacement, contact status and physiological characteristic of the finger 9 according to different operating modes, and to output encoded, sequenced and/or compressed finger displacement, contact status, physiological characteristic and mouse displacement. It is appreciated that the disposition of every element of the optical mouse 1 in FIG. 8 is only exemplary and not to limit the present disclosure.

Figure 9:
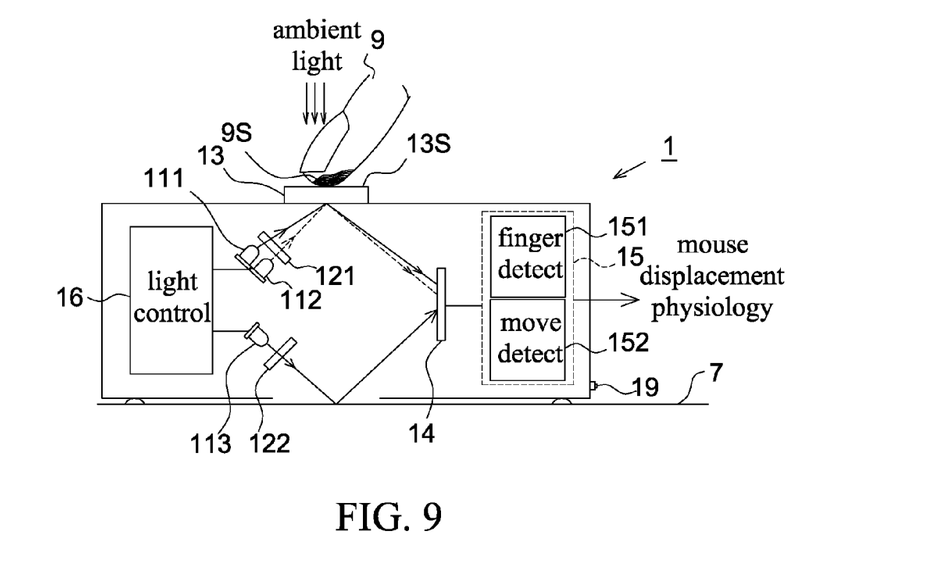

In an alternative embodiment, the optical mouse 1 may include the light sources 111-113, an image sensor 14, the processing unit 15 and the light control unit 16 as shown in FIG. 9. In the first mode, the light control unit 16 controls the light sources 111 and 112 to emit light; the image sensor 14 captures reflected light from the finger 9 to output image frames; and the processing unit 15 calculates the finger displacement, contact status and physiological characteristic according to the image frames. In the second mode, the light control unit 16 controls the light source 113 to emit light; the image sensor 14 captures reflected light from the work surface 7 to output image frames; and the processing unit 15 calculates the mouse displacement according to the image frames, wherein the methods of calculating the finger displacement, contact status and physiological characteristic have been described above and thus details thereof are not repeated herein. It is appreciated that the disposition of every element of the optical mouse 1 in FIG. 9 is only exemplary and not to limit the present disclosure. In this embodiment, the light control unit 16, the light sources 111 and 112, the image sensor 14 and the processing unit 15 (or the finger detection unit 151) are served as an optical finger mouse. The light control unit 16, the light source 113, the image sensor 14 and the processing unit 15 (or the displacement detection unit 152) are served as an optical navigation device, wherein the optical finger mouse and the optical navigation device may also be manufactured as a control chip, and a switching unit 19 is used to switch between two operating modes.

Figure 10:
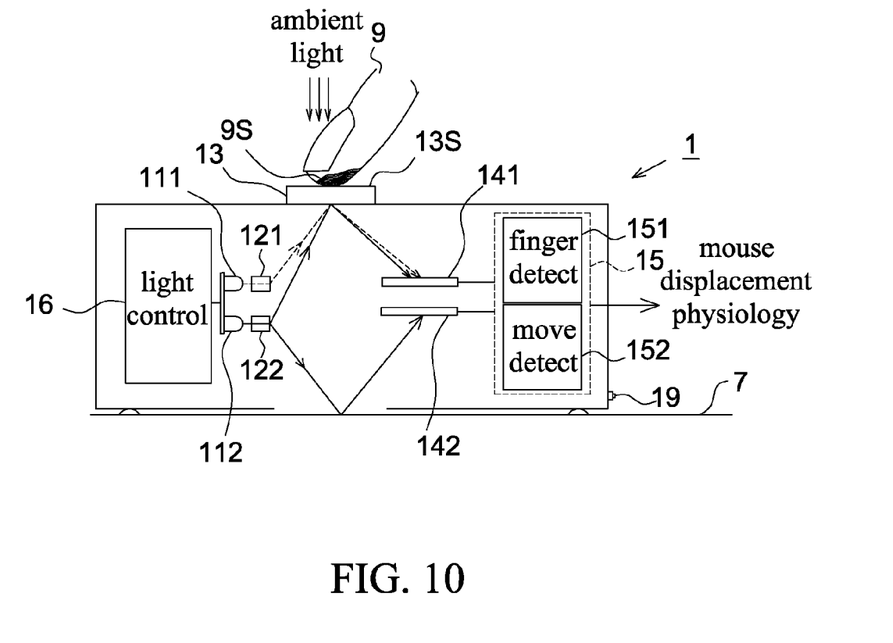

In an alternative embodiment, the optical mouse 1 may include two light sources 111-112, two light guides 121 and 122 (the number is only exemplary), two image sensors 141 and 142, the processing unit 15 and the light control unit 16 as shown in FIG. 10. The structure and the light guiding mechanism of the light guide 122 do not have any limitation as long as the light from the second light source 112 may be provided, through the light guide 122, to the touch member 13 and the work surface 7 simultaneously. In the first mode, the light control unit 16 controls the light sources 111 and 112 to emit light; the image sensor 141 captures reflected light from the finger 9 to output image frames; and the processing unit 15 calculates the finger displacement, contact status and physiological characteristic according to the image frames. In the second mode, the light control unit 16 controls the second light source 112 to emit light (the first light source 111 is disabled); the image sensor 142 captures reflected light from the work surface 7 to output image frames; and the processing unit 15 calculates the mouse displacement according to the image frames, wherein the methods of calculating the finger displacement, contact status and physiological characteristic have been described above and thus details thereof are not repeated herein. It is appreciated that the disposition of every element of the optical mouse 1 in FIG. 10 is only exemplary and not to limit the present disclosure. In this embodiment, the light control unit 16, the light sources 111 and 112, the image sensor 141 and the processing unit 15 (or the finger detection unit 151) are served as an optical finger mouse. The light control unit 16, the light source 112, the image sensor 142 and the processing unit 15 (or the displacement detection unit 152) are served as an optical navigation device, wherein the optical finger mouse and the optical navigation device may also be manufactured as a control chip, and a switching unit 19 is used to switch between two operating modes.

That is, the light source, the image sensor, the light control unit, the processing unit and the switching unit in FIGS. 9 and 10 may also be manufactured as a control chip or a package as shown in FIG. 8 so as to output encoded, sequenced and/or compressed finger displacement, contact status, physiological characteristic and mouse displacement. In other embodiments, said compression process may be performed by an additional compressing unit.

In a word, the operating method of the optical mouse according to the embodiment of the present disclosure is to use the switching unit 19 to switch between a first mode and a second mode and includes the steps of: in the first mode, calculating a contact status, a finger displacement and a physiological characteristic according to a plurality of image frames associated with the finger surface 9S using the optical mouse 1; and in the second mode, calculating a mouse displacement according to a plurality of image frames associated with the work surface 7 using the optical mouse 1.

As mentioned above, the conventional optical mouse can not detect the physiological characteristic of a user and the method of calculating the blood oxygenation for pulse oximeters cannot be applied to an optical mouse since it can not detect a moving object. Therefore, the present disclosure further provides an optical mouse (FIGS. 2A-2B and 8-10) that can detect both of the finger information and the mouse displacement information. The optical mouse in the embodiments of the present disclosure may detect a finger displacement and a physiological characteristic of a user simultaneously and may eliminate the signal noise caused by finger movement and the interference from ambient light sources, and further has the mechanisms of entering sleep mode and removing invalid physiology information.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. An optical mouse configured to detect a physiological characteristic of a finger or a mouse displacement of the optical mouse with respect to a work surface, the optical mouse comprising:
    a first light source configured to emit light of a first wavelength to the finger and a second light source configured to emit light of a second wavelength to the finger;
    a light control unit configured to control the first and second light sources;
    at least one image sensor configured to
        capture reflected light from the finger to generate a plurality of first image frames associated with the finger corresponding to on-states of the first light source and a plurality of second image frames associated with the finger corresponding to on-states of the second light source, and
        capture reflected light from the work surface to generate a plurality of image frames associated with the work surface; and
    a processing unit configured to
        divide each of the first image frames into at least two parts and calculate an average brightness of each part;
        analyze the average brightness of the each part of the first image frames to obtain a first intensity variation;
        divide each of the second image frames into at least two parts and calculate an average brightness of each part;
        analyze the average brightness of the each part of the second image frames to obtain a second intensity variation; and
        calculate the physiological characteristic according to the first intensity variation and the second intensity variation.

2. The optical mouse as claimed in claim 1, wherein the processing unit is further configured to calculate the mouse displacement according to the image frames associated with the work surface.

3. The optical mouse as claimed in claim 1, wherein the processing unit is further configured to calculate a heart rate according to a comparison result of comparing at least one pulse threshold with at least one of the first intensity variation and the second intensity variation.

4. The optical mouse as claimed in claim 1, wherein the light control unit is configured to alternatively enable the on-states of the first light source and the second light source such that the image sensor receives the reflected light associated with the first light source and the second light source alternatively.

5. The optical mouse as claimed in claim 1, further comprising a light guide configured to direct the light of the second wavelength emitted by the second light source to the finger and the work surface simultaneously.

6. The optical mouse as claimed in claim 1, further comprising a third light source configured to emit light of a third wavelength to the work surface, wherein the at least one image sensor comprises an image sensor configured to capture reflected light of the first wavelength and the second wavelength from the finger and reflected light of the third wavelength from the work surface.

7. The optical mouse as claimed in claim 1, further comprising a third light source configured to emit light of a third wavelength to the work surface, wherein the at least one image sensor comprises two image sensors respectively configured to capture (i) reflected light of the first wavelength and the second wavelength from the finger and (ii) reflected light of the third wavelength from the work surface.

8. The optical mouse as claimed in claim 1, wherein the first and second light sources, the light control unit, the at least one image sensor and the processing unit are packaged as a control chip to output the physiological characteristic and the mouse displacement processed by at least one of an encoding process, a sequential process and a compressing process.

9. The optical mouse as claimed in claim 1, wherein the processing unit is further configured to detect a contact status and a finger displacement according to the first or second image frames associated with the finger.

10. The optical mouse as claimed in claim 1, wherein
the light control unit is configured to simultaneously enable the on-states of the first light source and the second light source such that the image sensor receives the reflected light associated with the first light source and the second light source simultaneously, and
the image sensor comprises an optical filter covering at least a part of a sensing surface of the image sensor.

11. An operating method of an optical mouse switching between a first mode and a second mode using a switching unit, the operating method comprising:
in the first mode,
providing light of a first wavelength and a second wavelength to a finger surface;
capturing reflected light of the first wavelength to generate a plurality of first image frames and capturing reflected light of the second wavelength to generate a plurality of second image frames;
dividing each of the first image frames and each of the second image frames into at least two parts and calculating an average brightness of each part;
analyzing the average brightness of the each part of the first image frames to obtain a first intensity variation and analyzing the average brightness of the each part of the second image frames to obtain a second intensity variation; and
calculating a physiological characteristic according to the first intensity variation and the second intensity variation; and
in the second mode, calculating a mouse displacement according to a plurality of image frames associated with a work surface using the optical mouse.

12. The operating method as claimed in claim 11, wherein in the second mode the switching unit switches to the first mode when the mouse displacement is equal to zero over a predetermined time interval.

13. An optical mouse, comprising:
an optical finger mouse configured to detect at least one of a blood oxygenation and a heart rate of a user who has a finger operating the optical finger mouse, the optical finger mouse comprising:
a first light source configured to emit light of a first wavelength to the finger;
a second light source configured to emit light of a second wavelength to the finger;
a light control unit configured to control the first light source and the second light source:
an image sensor configured to receive reflected light from the finger at a sampling frequency to generate a plurality of first image frames corresponding to on-states of the first light source and a plurality of second image frames corresponding to on-states of the second light source; and
a processing unit configured to
divide each of the first image frames into at least two parts, calculate an average brightness of each part, and analyze the average brightness of the each part of the first image frames to obtain a first intensity variation;
divide each of the second image frames into at least two parts, calculate an average brightness of each part, and analyze the average brightness of the each part of the second image frames to obtain a second intensity variation; and
calculate at least one of the blood oxygenation and the heart rate according to the first intensity variation and the second intensity variation;
an optical navigation device configured to detect a mouse displacement of the optical mouse with respect to a work surface; and
a switching unit configured to switch the optical mouse to operate between the optical finger mouse and the optical navigation device.

14. The optical mouse as claimed in claim 13, wherein the light control unit is configured to alternatively enable the on-states of the first light source and the second light source such that the image sensor receives the reflected light associated with the first light source and the second light source alternatively.

15. The optical mouse as claimed in claim 13, wherein the optical finger mouse is further configured to
compare a brightness value of the first image frames and the second image frames with at least one brightness threshold to identify a contact status, and
calculate a finger displacement according to two of the first image frames, one of the first image frames and one of the second image frames, or two of the second image frames.

16. The optical mouse as claimed in claim 13, wherein the optical finger mouse and the optical navigation device are packaged as a control chip.

17. The optical mouse as claimed in claim 13, wherein
the light control unit is configured to simultaneously enable the on-states of the first light source and the second light source such that the image sensor receives the reflected light associated with the first light source and the second light source simultaneously, and
the image sensor comprises an optical filter covering at least a part of a sensing surface of the image sensor.

* * * * *